(12) United States Patent
Tsuda et al.

(10) Patent No.: US 12,144,617 B2
(45) Date of Patent: Nov. 19, 2024

(54) COMPONENT MEASUREMENT DEVICE AND COMPONENT MEASUREMENT METHOD

(71) Applicant: Mitsubishi Electric Corporation, Tokyo (JP)

(72) Inventors: Yuki Tsuda, Tokyo (JP); Shusaku Hayashi, Tokyo (JP); Koichi Akiyama, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 18/279,070

(22) PCT Filed: Mar. 3, 2021

(86) PCT No.: PCT/JP2021/008216
§ 371 (c)(1),
(2) Date: Aug. 28, 2023

(87) PCT Pub. No.: WO2022/185454
PCT Pub. Date: Sep. 9, 2022

(65) Prior Publication Data
US 2024/0122503 A1   Apr. 18, 2024

(51) Int. Cl.
*A61B 5/145* (2006.01)
*A61B 5/107* (2006.01)
*A61B 5/1455* (2006.01)

(52) U.S. Cl.
CPC ........ *A61B 5/14532* (2013.01); *A61B 5/1075* (2013.01); *A61B 5/1455* (2013.01)

(58) Field of Classification Search
CPC . A61B 5/1455; A61B 5/14532; A61B 5/1075; A61B 2562/0233
See application file for complete search history.

(56) References Cited

U.S. PATENT DOCUMENTS

2005/0065415 A1  3/2005  Cho et al.
2008/0068592 A1  3/2008  Uchida
(Continued)

FOREIGN PATENT DOCUMENTS

DE   11 2020 006 295 T5   11/2022
JP        2005-095317 A    4/2005
(Continued)

OTHER PUBLICATIONS

Motoji Takahashi, "Progress in skin bioengineering technique and its application to percutaneous absorption", Drug Delivery System, vol. 22, No. 4, 2007, pp. 433-441 (17 pages including Partial English Translation).

(Continued)

*Primary Examiner* — Eric F Winakur
(74) *Attorney, Agent, or Firm* — XSENSUS LLP

(57) ABSTRACT

A component measurement device for measuring a given component contained in a sample. The component measurement device includes an excitation light source to emit excitation light onto the optical medium portion, a probe light source to emit probe light onto the optical medium portion, an intensity modulation unit to perform intensity modulation on the excitation light emitted by the excitation light source based on stratum corneum information about stratum corneum of the sample to generate intensity-modulated excitation light and emit the generated intensity-modulated excitation light onto the optical medium portion, and a measurement unit to measure the given component based on a difference between the probe light emitted from the optical medium portion in a first state where the excitation light is emitted and the probe light emitted from the optical medium portion in a second state where the intensity-modulated excitation light is emitted.

11 Claims, 2 Drawing Sheets

(56) References Cited

U.S. PATENT DOCUMENTS

| | | |
|---|---|---|
| 2017/0146455 A1 | 5/2017 | Mäntele et al. |
| 2018/0306726 A1 | 10/2018 | Mannhardt et al. |
| 2018/0328835 A1 | 11/2018 | Bauer et al. |
| 2018/0335381 A1 | 11/2018 | Bauer et al. |
| 2020/0170553 A1 | 6/2020 | Kasahara et al. |
| 2020/0408686 A1 | 12/2020 | Ogawa |
| 2021/0059574 A1 | 3/2021 | Shinohara et al. |
| 2022/0404275 A1 | 12/2022 | Hayashi et al. |
| 2023/0053065 A1 | 2/2023 | Tsuda et al. |
| 2023/0181063 A1* | 6/2023 | Mäntele ............... A61B 5/1455 600/301 |

FOREIGN PATENT DOCUMENTS

| | | |
|---|---|---|
| JP | 2008-237775 A | 10/2008 |
| JP | 2014-140423 A | 8/2014 |
| JP | 2017-519214 A | 7/2017 |
| JP | 2019-037752 A | 3/2019 |
| JP | 2019-507319 A | 3/2019 |
| JP | 6786027 B1 | 11/2020 |
| WO | 2006/051778 A1 | 5/2006 |
| WO | 2015/193310 A1 | 12/2015 |
| WO | 2019/150543 A1 | 8/2019 |
| WO | 2019/176157 A1 | 9/2019 |

OTHER PUBLICATIONS

Webb et. al., "Thermal Transport Characteristics of Human Skin Measured In Vivo Using Ultrathin Conformal Arrays of Thermal Sensors and Actuators", PLOS One | DOI:10.1371/journal.pone.0118131, Feb. 6, 2015, pp. 1-17.

Decision to Grant mailed on Sep. 21, 2021, received for JP Application 2021-532470, 7 pages including English Translation.

International Search Report and Written Opinion mailed on May 11, 2021, received for PCT Application PCT/JP2021/008216, filed on Mar. 3, 2021, 10 pages including English Translation.

Office Action issued on Jan. 27, 2024, in corresponding Chinese patent Application No. 202180094819.7, 17 pages.

Office Action issued Jul. 18, 2024 in corresponding Chinese Patent Application No. 202180094819.7 (16 pgs).

Office Action issued Jun. 6, 2024 in counterpart German Application No. 11 2021 006 621.8 (12 pgs).

\* cited by examiner

COMPONENT MEASUREMENT DEVICE AND COMPONENT MEASUREMENT METHOD

CROSS-REFERENCE TO RELATED APPLICATION

This application is based on PCT filing PCT/JP2021/008216, filed Mar. 3, 2021, the entire contents of which are incorporated herein by reference.

TECHNICAL FIELD

The present invention relates to a component measurement device and a component measurement method, and specifically relates to a component measurement device and component measurement method for measuring a component in a living body.

BACKGROUND ART

In applications to various fields, particularly to chemistry, biology, and medical science, a component measurement device for measuring a component contained in a sample is known. For example, a component measurement device for measuring a component contained in a living body is known. Most of component measurement devices are invasive devices using chemical analysis. In the case of such an invasive component measurement device, a substance changes due to partial separation or chemical reaction during measurement. For example, for measurement of a blood glucose level in a living body, an invasive sensor is widely used. In this case, blood is sampled using a needle and is reacted with a reagent.

When an invasive component measurement device is used for, for example, blood glucose level measurement, a patient feels pain due to needling. Therefore, particularly in the fields of medical science and health care, there have been demands for non-invasive component measurement devices.

A non-invasive component measurement device based on optothermal spectroscopy is known which performs measurement based on interstitial fluid to which biological components are to be transported from blood. For example, Patent Literature 1 discloses a non-invasive component measurement device to perform, as biometric measurement, measurement of a component such as blood glucose level or lipid based on interstitial fluid to which biological components are to be transported from blood. Interstitial fluid is fluid that is contained in cells and is present also in an area closer to the skin surface than the blood vessels, and is therefore suitable for use in measurement from outside of the body.

CITATION LIST

Patent Literature

PTL1: Japanese National Patent Publication No. 2017-519214

SUMMARY OF INVENTION

Technical Problem

However, stratum corneum that is the outermost surface of the skin is a layer of dead cells. Interstitial fluid is not contained in stratum corneum that is the outermost surface of the skin as a layer of dead cells, and is present in stratum *granulosum* under stratum corneum and in layers deeper than stratum *granulosum*. The thickness of stratum corneum generally depends on the part of a living body, and may be different between a part such as an arm, wrist, forehead, or abdomen and a part that frequently comes into contact with external substances, such as a finger, palm, or feet bottom. Therefore, in the case of such a non-invasive component measurement device as described above to perform measurement based on interstitial fluid, measurement may be performed on the basis of information from a portion containing no interstitial fluid. For this reason, such a non-invasive component measurement device as described above is required to be improved in component measurement accuracy.

In order to solve the above problem, it is an object of the present invention to provide a non-invasive component measurement device and component measurement method having improved component measurement accuracy.

Solution to Problem

A component measurement device according to one aspect of the present invention is a component measurement device for measuring a given component contained in a sample, the component measurement device including: an optical medium portion on which the sample is stationarily placed; an excitation light source to emit excitation light onto the optical medium portion; a probe light source to emit probe light onto the optical medium portion; an intensity modulation unit to perform intensity modulation on the excitation light emitted by the excitation light source based on stratum corneum information about stratum corneum of the sample to generate intensity-modulated excitation light and emit the generated intensity-modulated excitation light onto the optical medium portion; and a measurement unit to measure the given component based on a difference between the probe light emitted from the optical medium portion in a first state where the excitation light is emitted and the probe light emitted from the optical medium portion in a second state where the intensity-modulated excitation light is emitted.

A component measurement method according to one aspect of the present invention is a component measurement method for measuring a given component contained in a sample, the component measurement method including: a stationarily placing step of stationarily placing the sample on an optical medium portion, an excitation light emitting step of emitting excitation light from an excitation light source onto the optical medium portion, a probe light emitting step of emitting probe light from a probe light source onto the optical medium portion, a stratum corneum information acquisition step of acquiring stratum corneum information about stratum corneum of the sample, an intensity modulation step of performing intensity modulation on the excitation light emitted by the excitation light source based on the stratum corneum information acquired in the stratum corneum information acquisition step to generate intensity-modulated excitation light and emit the generated intensity-modulated excitation light onto the optical medium portion, and a measurement step of measuring the given component based on a difference between the probe light emitted from the optical medium portion in a first state where the excitation light is emitted and the probe light emitted from the optical medium portion in a second state where the intensity-modulated excitation light is emitted.

Advantageous Effects of Invention

According to one aspect of the present invention, it is possible to provide a non-invasive component measurement device and component measurement method having improved component measurement accuracy.

DESCRIPTION OF EMBODIMENTS

Hereinbelow, an example of a component measurement device for measuring a blood glucose level in a living body as a component contained in a sample will be described with reference to the drawings. However, needless to say, the component measurement device according to the present invention can be applied also to measurement of a component other than blood glucose level.

First Embodiment

Figure 1:
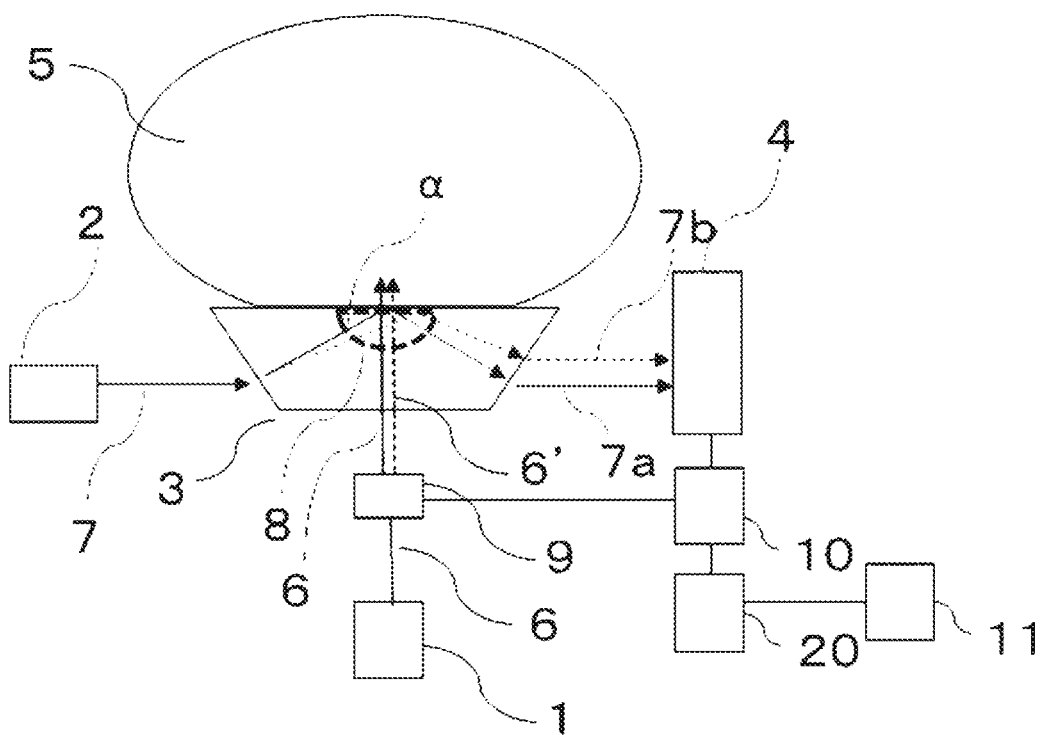
FIG. 1 is a diagram showing the configuration of a component measurement device according to a first embodiment.

FIG. 1 is a diagram showing the configuration of a component measurement device 100 according to a first embodiment. Component measurement device 100 according to the first embodiment includes an excitation light source 1, a probe light source 2, an optical medium portion 3, a light position detector 4, an optical chopper 9, a lock-in amplifier 10, a stratum corneum information acquisition unit 11, and an operation unit 20.

Excitation light source 1 includes at least one infrared light source. Excitation light source 1 is a component to emit, as excitation light 6, infrared light in the entire wavelength range from 8 μm to 10 μm including the wavelength of a fingerprint spectrum by which glucose can be identified to measure a blood glucose level or in part of such a wavelength range. Excitation light source 1 includes a broadband quantum cascade laser. Excitation light source 1 is configured to include wavelengths used for measurement, such as wavelengths λ1 and λ2 absorbed by glucose in a human body and a wavelength λ3 not absorbed by glucose in a human body and used as a reference wavelength. Excitation light source 1 may be configured to include 4 or more wavelengths used for measurement.

Probe light source 2 is a laser to output, as probe light 7, light in a wavelength range that passes through optical medium portion 3 that will be described later. Probe light source 2 is preferably configured as a laser to output light having a wavelength in a wavelength range from visible light to near-infrared. This is because light having a wavelength in a wavelength range from visible light to near-infrared is easily generated for output and detected, and therefore the burden of assembling component measurement device 100 can be reduced.

Optical medium portion 3 is a sample stage on which a sample 5 containing glucose used to measure a blood glucose level is stationarily placed. In component measurement device 100 of the first embodiment according to an example of the present invention, a finger is stationarily placed as sample 5 on optical medium portion 3 as a sample stage. Optical medium portion 3 is formed using, as an optical medium, a material that is highly permeable to light in the infrared wavelength range, such as zinc sulfide (ZnS), zinc selenide (ZnSe), germanium (Ge), silicon (Si), or chalcogenide glass so as to have a predetermined refractive index gradient 8. Refractive index gradient 8 is changed by excitation light 6 emitted by excitation light source 1.

Light position detector 4 is a light detection sensor to detect light from probe light source 2 emitted from optical medium portion 3. By such detection, light position detector 4 detects the pathway of light emitted from probe light source 2 and passed through optical medium portion 3. Light position detector 4 is configured to be able to detect emitted probe light 7a and emitted probe refracting light 7b which will be described later. Light position detector 4 detects the position of light entering light position detector 4. Light position detector 4 is configured using, for example, a quadrant photodiode.

Optical chopper 9 is a component to perform intensity modulation on light passing therethrough using a specific frequency component. Optical chopper 9 is disposed between excitation light source 1 and optical medium portion 3 and is configured to perform intensity modulation on excitation light 6 emitted from excitation light source 1 and send intensity-modulated excitation light 6' to optical medium portion 3. Optical chopper 9 includes a rotary blade. The rotation of the rotary blade periodically blocks excitation light 6 as continuous light so that intensity modulation is performed on excitation light 6.

Refractive index gradient 8 of optical medium portion 3 at the time when excitation light 6 not subjected to intensity modulation is emitted is different from refractive index gradient 8 of optical medium portion 3 at the time when intensity-modulated excitation light 6' is emitted. Light position detector 4 detects a difference between the pathway of emitted probe light 7a at the time when excitation light 6 not subjected to intensity modulation is emitted and the pathway of emitted probe refracting light 7b at the time when intensity-modulated excitation light 6' is emitted.

Lock-in amplifier 10 is connected to light position detector 4 and optical chopper 9. Lock-in amplifier 10 reads, among signals measured by light position detector 4, a signal synchronized with the modulation frequency component of excitation light 6. Therefore, component measurement device 100 can perform measurement with high accuracy.

A measured signal includes a noise including various frequency components, and the amount of noise increases as the frequency reduces. When excitation light is modulated using an optical chopper to have a frequency f, a desired measured signal is a modulated signal that is the same as modulated excitation light in frequency and phase but different in amplitude from the modulated excitation light. At this time, when the excitation light and the measured signal are multiplied, a signal is obtained which has a frequency component obtained by performing addition (2f) on their respective frequency components f and a frequency component obtained by subtraction (0=direct current component) on their respective frequency components f. When the measured signal includes a noise including a large amount of different frequency components, measured signals corresponding to the modulation frequency of excitation light and the frequency of a noise are added. However, a necessary component is contained only in a direct current component. Therefore, only a direct current component is measured using a low-pass filter, which makes it possible to remove a noise component even from a weak signal to perform measurement with high accuracy.

Stratum corneum information acquisition unit 11 is a component to acquire stratum corneum information about the stratum corneum of sample 5 stationarily placed on optical medium portion 3. For example, stratum corneum information acquisition unit 11 is an input device to acquire stratum corneum information input by a user of component measurement device 100.

The thickness of stratum corneum may be different depending on a measurement method used or from person to person in a precise sense, but can generally depend on the part of a living body. It is known that the stratum corneum of a part that frequently comes into contact with external substances, such as a finger, palm, or feet bottom, is as thick as 100 to 300 μm whereas the thickness of stratum corneum of a part such as an arm, wrist, forehead, or abdomen is about 20 μm. Therefore, stratum corneum information acquisition unit 11 according to the first embodiment is a numeric input device such as a numeric keyboard and acquires, as stratum corneum information, a thickness value such as 20 μm from a user.

As Stratum corneum information acquisition unit 11 according to an example of the present invention described above, a numeric input device is exemplified. However, the present invention is not limited to this example. An input device may be used which can select a target part corresponding to sample 5 from among parts such as an arm, wrist, forehead, abdomen, finger, palm, and feet bottom. The thickness value of stratum corneum corresponding to each part such as an arm, wrist, forehead, abdomen, finger, palm, or feet bottom may be stored in a memory unit so that the thickness value corresponding to a part selected using stratum corneum information acquisition unit 11 can be acquired. Such a configuration makes it possible to increase design flexibility of component measurement device 100.

Operation unit 20 is a component to calculate a blood glucose level to measure glucose contained in sample 5. Operation unit 20 is connected to lock-in amplifier 10. Operation unit 20 calculates a blood glucose level based on a signal acquired by lock-in amplifier 10.

Operation unit 20 is also a component to further perform adjustment based on the stratum corneum of sample 5. Operation unit 20 is connected not only to lock-in amplifier 10 but also to stratum corneum information acquisition unit 11. Operation unit 20 performs intensity modulation on excitation light 6 emitted from excitation light source 1 based on stratum corneum information acquired by stratum corneum information acquisition unit 11. Specifically, operation unit 20 controls the rotation speed of optical chopper 9 to set a modulation frequency that will be described later. The modulation frequency herein means the frequency of intensity modulation of excitation light 6.

As shown in FIG. 1, component measurement device 100 is configured so that probe light 7 emitted from probe light source 2 enters optical medium portion 3 as incident probe light and is emitted toward light position detector 4 as emitted probe light 7a. When excitation light source 1 emits excitation light 6 toward optical medium portion 3 so that absorption heat is generated in sample 5, the generated absorption heat is conducted to optical medium portion 3 so that a temperature gradient is formed in optical medium portion 3 and refractive index gradient 8 of optical medium portion 3 changes. When passing through optical medium portion 3 whose refractive index gradient 8 has been changed, probe light 7 is emitted toward light position detector 4 as emitted probe refracting light 7b whose light path is different from that of emitted probe light 7a because the refractive index of optical medium portion 3 also changes due to a change in refractive index gradient 8. Component measurement device 100 is configured to perform component measurement by allowing light position detector 4 to detect a gap between emitted probe light 7a and emitted probe refracting light 7b and allowing operation unit 20 to perform an operation on a detection result passed through lock-in amplifier 10. Above-described light position detector 4, lock-in amplifier 10, operation unit 20, and a combination thereof relate to an example of a measurement unit to measure a given component based on a difference between emitted probe light 7a emitted from optical medium portion 3 at the time when excitation light 6 is emitted and emitted probe refracting light 7b emitted from optical medium portion 3 at the time when intensity-modulated excitation light 6' is emitted.

Optical chopper 9 performs intensity modulation based on the modulation frequency set by operation unit 20 so that excitation light 6 emitted from excitation light source 1 has a modulation frequency corresponding to stratum corneum information acquired by stratum corneum information acquisition unit 11. Specifically, intensity modulation is performed on excitation light 6 by rotating the rotary blade at a rotation speed corresponding to the modulation frequency set by operation unit 20. That is, optical chopper 9 corresponds to an example of an intensity modulation unit according to the present invention. Intensity-modulated excitation light 6' after passing through optical chopper 9 passes through optical medium portion 3 and enters sample 5. In the case of blood glucose level measurement, sample 5 corresponds to a part of a subject, such as a finger, wrist, arm or earlobe. Operation unit 20 calculates absorption by a glucose component contained in interstitial fluid of sample 5 where probe light 7 enters through the skin.

Figure 2:
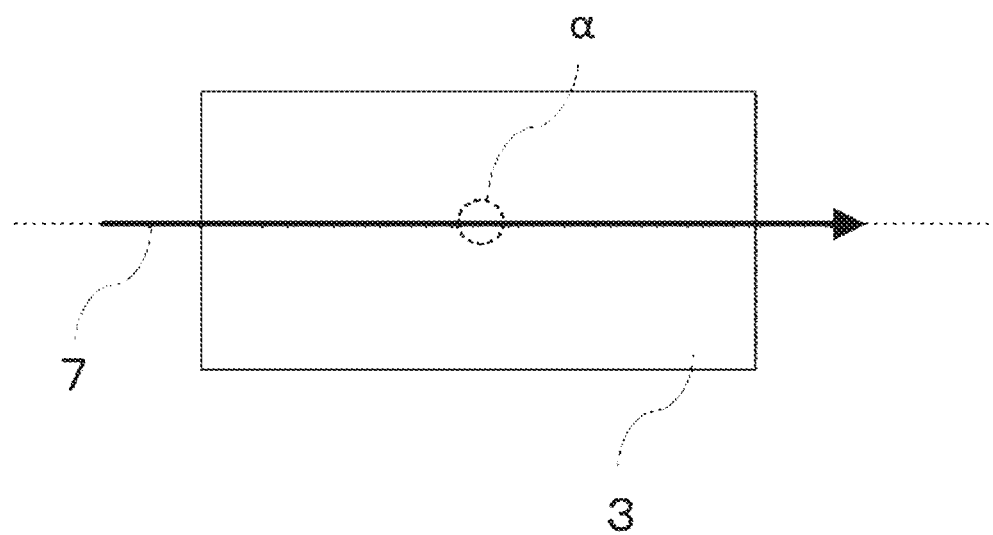
FIG. 2 is a top view of an optical medium portion of the component measurement device according to the first embodiment.

FIG. 2 is a top view of optical medium portion 3 of component measurement device 100 according to the first embodiment. Excitation light source 1 and probe light source 2 are configured so that the light path of probe light 7 intersects excitation light 6 from excitation light source 1 in an excitation light radiation site on the plan view shown in FIG. 2. When the range of a refractive index gradient generation area α generated in optical medium portion 3 is taken into consideration, the beam width of excitation light 6 emitted by excitation light source 1 is preferably the same as or greater than that of probe light 7 emitted by probe light source 2. If the beam width of excitation light 6 is small, the refractive index gradient generation area α may be smaller than the beam width of probe light 7. If the refractive index gradient generation area α is smaller than the beam width of probe light 7, only part of probe light Z is influenced, which makes it difficult to measure a change in the light path of probe light 7. On the other hand, if the beam width of excitation light 6 is excessively large, the density of excitation light 6 may reduce or the refractive index gradient generation area α may widen. If the density of excitation light 6 is lower than necessary or the refractive index gradient generation area α is wider than necessary, the refractive index gradient itself may reduce. If the refractive index gradient itself reduces, the refractive index gradient may have no effect of changing the light path of probe light 7. Therefore, specifically, it is preferred that the beam width of excitation light 6 is 50 μm and the beam width of probe light Z is 30 μm.

The operation of blood glucose level measurement in component measurement device 100 will be described. The description will be made with reference to a case where a state where light output of excitation light source 1 is zero is defined as a reference state. In the reference state, the internal state of optical medium portion 3 is considered to be uniform. Therefore, probe light 7 output from the probe light source 2 is refracted only when entering and exiting optical medium portion 3. Here, a position where emitted probe light 7a enters light position detector 4 in the reference state is defined as a reference position. In an example according to the first embodiment, as shown in FIG. 1, component measurement device 100 is configured so that probe light 7 is totally reflected once by the contact surface with sample 5 at the excitation light radiation site. Refractive index gradient 8 generated in an optical medium that will be described later is generated near the surface of optical medium portion 3, and particularly, the gradient is larger as it is closer to the surface in contact with an area where heat is generated. As described above, since the probe light source is disposed, the incidence angle of probe light 7 can be made shallow, and therefore the pathway through which probe light 7 passes is located near the surface of the optical medium. This makes it possible to efficiently change the light path. Probe light 7 is refracted by passing through refractive index gradient 8 so that its light path changes. Therefore, for example, component measurement device 100 may be configured so that the pathway is one such that probe light 7 is totally reflected twice or more in optical medium portion 3 or probe light 7 passes near the contact surface with sample 5 in parallel with the contact surface.

After probe light source 2 emits probe light 7, excitation light source 1 outputs, as excitation light 6, infrared light with a fingerprint spectrum wavelength of glucose. Optical chopper 9 performs intensity modulation on excitation light 6 output by excitation light source 1. Excitation light 6 subjected to intensity modulation by optical chopper 9 passes through optical medium portion 3 and enters sample 5. Excitation light 6 that is infrared light and has entered sample 5 is absorbed by glucose contained in interstitial fluid present near the surface of sample 5. When excitation light 6 is absorbed by glucose, absorption heat is generated inside sample 5. The generated absorption heat is conducted to optical medium portion 3 from sample 5. When the absorption heat is conducted to optical medium portion 3, a temperature gradient is generated in optical medium portion 3. The refractive index of optical medium portion 3 generally has temperature dependency. Therefore, when a temperature gradient is generated in optical medium portion 3, a refractive index gradient is generated so that refractive index gradient 8 is formed. The following description will be made with reference to a case where a state where refractive index gradient 8 is formed is defined as a state A.

When excitation light 6 emitted onto sample 5 penetrates up to about 50 to 100 μm inside sample 5 so that absorption heat is generated, heat diffusion length L, which is the length of diffusion of generated heat, is represented by the following formula (1) using the frequency f which corresponds to the modulation frequency of excitation light 6 and at which absorption heat is generated and the thermal diffusion coefficient α of sample 5. When sample 5 is a part of a subject, such as a finger, wrist, arm, or earlobe, the thermal diffusion coefficient of skin of such a part is about 0.13 to 0.17 mm²/s.

$$L=\sqrt{\beta/(\pi \cdot f)} \qquad \text{Formula (1)}$$

Figure 3:
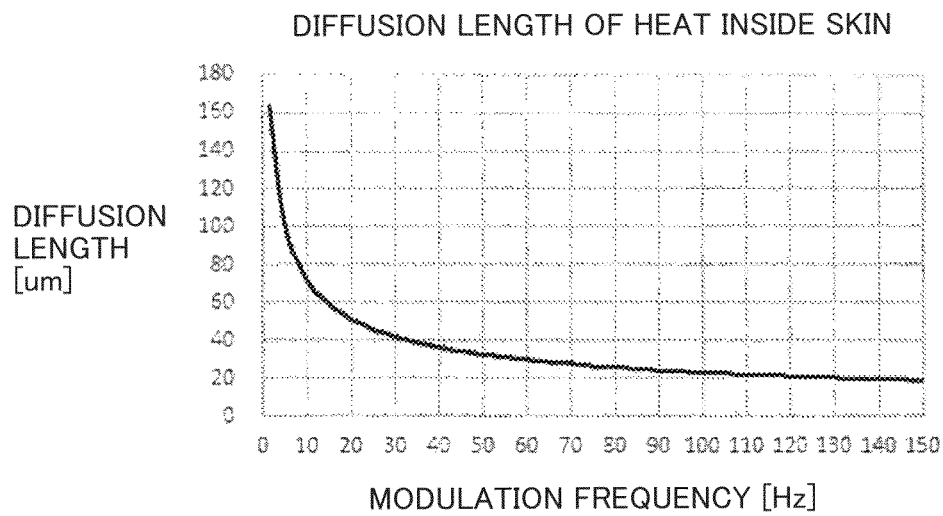
FIG. 3 is a graph showing the relationship between a modulation frequency used for measurement and a diffusion length of heat generated inside the skin.

FIG. 3 is a graph showing the relationship between a modulation frequency used for measurement and a diffusion length of heat generated inside the skin. FIG. 3 shows the heat diffusion length inside the skin with respect to the modulation frequency when the thermal diffusion coefficient is 0.15 mm²/s. Specifically, when the modulation frequency is 100 Hz, 30 Hz, or 5 Hz, the heat diffusion length is about 20 μm, about 40 μm, and about 100 μm, respectively. In order to measure a component contained in interstitial fluid, the heat diffusion length needs to be larger than the thickness of stratum corneum. Therefore, the modulation frequency f is set to satisfy $f<\alpha/(d^2 \cdot \pi)$. More preferably, the heat diffusion length is in the range of one to three times the thickness of stratum corneum, and therefore the modulation frequency f is set to satisfy $\alpha/\{(3d)^2 \cdot \pi\}<f<\alpha/(d^2 \cdot \pi)$. In order to increase the heat diffusion length, the modulation frequency needs to be reduced. However, noise generated during measurement is usually greater in a lower frequency range. Therefore, when the modulation frequency is low, the S/N ratio of a signal may be reduced even using a lock-in amplifier. For this reason, the frequency to be used is preferably as high as possible in a range such that interstitial fluid can be measured. Specifically, when a finger or palm whose skin has a thick stratum corneum of 100 μm or more is measured, operation unit 20 sets the rotation speed of optical chopper 9 via lock-in amplifier 10 so that the modulation frequency of excitation light 6 is 0.5 to 5 Hz. Similarly, when a part, such as an arm, wrist, or forehead, whose skin has a stratum corneum of about 20 μm is measured, operation unit 20 sets the rotation speed of optical chopper 9 via lock-in amplifier 10 so that the modulation frequency of excitation light 6 is 15 to 100 Hz. Such a configuration as described above makes it possible, when stratum corneum is relatively thin, to perform measurement using a higher modulation frequency.

When passing through refractive index gradient 8 in which the gradient of refractive index is not generated in the reference state, probe light 7 is refracted according to a refractive index at a position in optical medium portion 3 where probe light 7 passes. Refracting probe light 7 is emitted from optical medium portion 3 as emitted probe light 7a and enters light position detector 4. In the reference state, the light position detector 4 detects a position where emitted probe light 7a enters light position detector 4 as a reference position.

When passing through refractive index gradient 8 in which the gradient of refractive index is generated in the state A, probe light 7 is refracted according to a refractive index in refractive index gradient 8 at a position in optical medium portion 3 where probe light 7 passes. Refracting incident probe light 7 is emitted from optical medium portion 3 as emitted probe refracting light 7b and enters light position detector 4. In the state A, the light position detector 4 detects a position where emitted probe refracting light 7b enters light position detector 4 as a displaced position.

Lock-in amplifier 10 reads the value of a signal based on a difference between the reference position and the displaced position detected by light position detector 4. Operation unit 20 acquires the signal about the difference read by lock-in amplifier 10 and calculates a blood glucose level as a component.

As described above, component measurement device 100 according to the first embodiment can efficiently measure absorption heat generated by a given component in interstitial fluid contained in layers deeper than stratum corneum by driving optical chopper 9 based on stratum corneum information acquired by stratum corneum information acquisition unit 11. Specifically, the diffusion length of heat generated in a living body during measurement is about 1 to 3 times the thickness of stratum corneum, and therefore absorption heat generated by a glucose component in interstitial fluid contained in layers deeper than stratum corneum can efficiently be measured. In other words, it is possible to provide a non-invasive component measurement device which reduces the risk of performing measurement on the basis of information from a portion containing no interstitial fluid and therefore achieves improved component measurement accuracy.

A component measurement method for measuring a blood glucose level as a given component contained in sample 5 will be described using component measurement device 100 according to the first embodiment. In the component measurement method, a stationarily placing step is first performed in which sample 5 is stationarily placed on optical medium portion 3. In the component measurement method, after the stationarily placing step is performed, an excitation light emitting step is performed in which excitation light 6 is emitted from excitation light source 1 onto optical medium portion 3. In the component measurement method, after the stationarily placing step is performed, a probe light emitting step is also performed in which probe light 7 is emitted from probe light source 2 onto optical medium portion 3. In the component measurement method, a stratum corneum information acquisition step is also performed in which stratum corneum information about the stratum corneum of sample 5 is acquired.

In the component measurement method described above, after stratum corneum information is acquired in the stratum corneum information acquisition step, an intensity modulation step is performed in which intensity modulation is performed on excitation light 6 emitted by excitation light source 1 based on the acquired stratum corneum information to generate intensity-modulated excitation light and the generated intensity-modulated excitation light is emitted onto optical medium portion 3. In the component measurement method, after the intensity modulation step is performed, a measurement step is performed in which a blood glucose level as a given component is measured based on a difference between emitted probe light 7a emitted from optical medium portion 3 at the time when excitation light 6 is emitted and emitted probe refracting light 7b emitted from optical medium portion 3 at the time when the intensity-modulated excitation light is emitted.

As described above, the component measurement method according to the first embodiment performs the intensity modulation step by driving optical chopper 9 based on the stratum corneum information acquired by stratum corneum information acquisition unit 11, which makes it possible to efficiently measure absorption heat generated by a given component in interstitial fluid contained in layers deeper than stratum corneum. Specifically, the diffusion length of heat generated in a living body during measurement is about 1 to 3 times the thickness of stratum corneum, and therefore absorption heat generated by a glucose component in interstitial fluid contained in layers deeper than stratum corneum can efficiently be measured. In other words, it is possible to provide a non-invasive component measurement method which reduces the risk of performing measurement on the basis of information from a portion containing no interstitial fluid and therefore achieves improved component measurement accuracy.

In the above-described first embodiment, an example of component measurement device 100 to calculate a blood glucose level has been described. However, the present invention is not limited to such an example described above. For example, the component measurement device according to the present invention may be one to measure and calculate protein, amino acid, sugar, fatty acid, hormone, neurotransmitter, or the like contained in interstitial fluid of a living body. Therefore, the component measurement device according to the present invention can be applied to measurement of various biological information.

Second Embodiment

Figure 4:
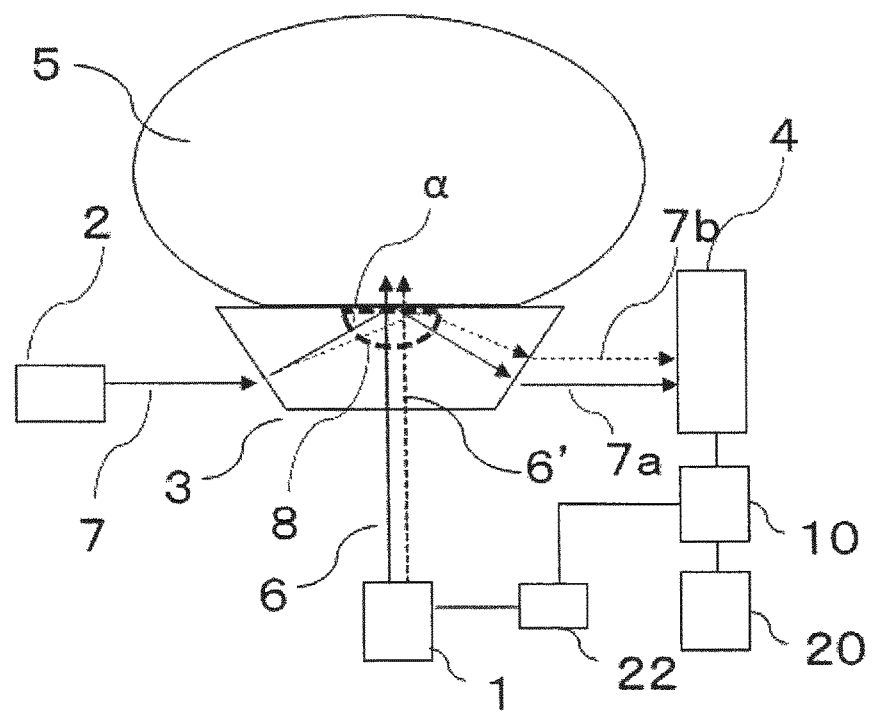
FIG. 4 is a diagram showing the configuration of a component measurement device according to a second embodiment.

FIG. 4 is a diagram showing the configuration of a component measurement device 101 according to a second embodiment. Component measurement device 101 according to the second embodiment is different from component measurement device 100 according to the first embodiment in that optical chopper 9 is not provided. Component measurement device 101 according to the second embodiment includes, instead of optical chopper 9, a modulator 22 to perform modulation on a power source of excitation light source 1. In component measurement device 101 according to the second embodiment, modulator 22 periodically sends a modulated signal to excitation light source 1 to perform intensity modulation on excitation light 6. That is, modulator 22 corresponds to an example of the intensity modulation unit according to the present invention.

Modulator 22 is configured using, for example, a signal generator to output an intensity-modulated pulse signal according to a set frequency. However, the present invention is not limited to this example. A device capable of modulating an electric signal may be used. Signal modulation may be performed using a periodic function such as a sine wave, a square wave, or a saw-tooth wave. The power source of excitation light source 1 supplies power to excitation light source 1 by current output or voltage output modulated according to the signal of modulator 22. However, the present invention is not limited to this example. A configuration in which a power source having a modulation function is integrated with modulator 22 may be used.

In component measurement device 101 according to the second embodiment, lock-in amplifier 10 is connected to modulator 22. Modulator 22 determines the operation frequency of the lock-in amplifier 10 so that the modulation frequency of excitation light source 1 and the operation frequency of the lock-in amplifier 10 are synchronized with each other. The other configuration of component measurement device 101 is the same as that of component measurement device 100 according to the first embodiment.

Component measurement device 101 according to the second embodiment is different from component measurement device 100 according to the first embodiment in that optical chopper 9 is not provided. Therefore, the modulation frequency can be measured without using a physical drive mechanism to externally perform laser intensity modulation. This makes it possible to provide a non-invasive component measurement device which not only reduces the risk of performing measurement on the basis of information from a portion containing no interstitial fluid and achieves improved component measurement accuracy but also can be reduced in size by space-saving.

REFERENCE SIGNS LIST

1: excitation light source, 2: probe light source, 3: optical medium portion, 4: light position detector, 5: sample, 6:

excitation light, 7: probe light, 7a: emitted probe light, 7b: emitted probe refracting light, 8: refractive index gradient, 9: optical chopper, 10: lock-in amplifier, 11: stratum corneum information acquisition unit, 20: operation unit, 22: modulator, 100, 101: component measurement device

The invention claimed is:

1. A component measurement device for measuring a given component contained in a sample, the component measurement device comprising:
    an optical medium portion on which the sample is stationarily placed;
    an excitation light source to emit excitation light onto the optical medium portion;
    a probe light source to emit probe light onto the optical medium portion;
    a stratum corneum information acquisition circuitry to acquire stratum corneum information about a stratum corneum of the sample,
    an intensity modulator to perform intensity modulation on the excitation light emitted by the excitation light source based on the stratum corneum information about the stratum corneum of the sample acquired by the stratum corneum information acquisition circuitry to generate intensity-modulated excitation light such that the generated intensity-modulated excitation light is emitted onto the optical medium portion;
    a light position detector to detect a difference between the probe light emitted from the optical medium portion in a first state where the excitation light is emitted and the probe light emitted from the optical medium portion in a second state where the intensity-modulated excitation light is emitted; and
    an operation processor configured to measure the given component based on the detected difference.

2. The component measurement device according to claim 1, wherein:
    when a modulation frequency of the intensity-modulated excitation light is defined as f, a thickness of the stratum corneum indicated by the stratum corneum information acquired by the stratum corneum information acquisition circuitry is defined as d, and a thermal diffusion coefficient of the sample is defined as $\alpha$, the operation processor is configured to control the intensity modulator to perform the intensity modulation so that f, d, and $\alpha$ satisfy $f<\alpha/(d^2\pi)$.

3. The component measurement device according to claim 2, wherein:
    the operation processor is configured to control the intensity modulator to perform the intensity modulation so that f, d, and $\alpha$ further satisfy $\alpha/\{(3d)^2\pi\}<f$.

4. The component measurement device according to claim 1, wherein:
    the intensity modulator includes a rotary blade that rotates at a predetermined rotation speed,
    the intensity modulator is disposed between the excitation light source and the optical medium portion,
    the excitation light source is configured to emit the excitation light onto the optical medium portion through the rotary blade, and
    the operation processor is configured to change the rotation speed of the rotary blade based on the stratum corneum information acquired by the stratum corneum information acquisition circuitry.

5. The component measurement device according to claim 1, wherein:
    the intensity modulator includes a modulator to perform modulation on a power source of the excitation light source, and
    the operation processor is configured to change the modulation performed by the modulator based on the stratum corneum information acquired by the stratum corneum information acquisition circuitry.

6. A component measurement method for measuring a given component contained in a sample, the component measurement method comprising:
    emitting excitation light from an excitation light source onto an optical medium portion which has the sample stationarily placed thereon,
    emitting probe light from a probe light source onto the optical medium portion,
    performing intensity modulation on the excitation light emitted by the excitation light source based on stratum corneum information about a stratum corneum of the sample to generate intensity-modulated excitation light,
    emitting the generated intensity-modulated excitation light onto the optical medium portion,
    detecting a difference between the probe light emitted from the optical medium portion in a first state where the excitation light is emitted and the probe light emitted from the optical medium portion in a second state where the intensity-modulated excitation light is emitted, and
    measuring the given component based on the detected difference.

7. The component measurement method according to claim 6, further comprising acquiring the stratum corneum information about the stratum corneum of the sample.

8. The component measurement method according to claim 6, wherein:
    when a modulation frequency of the intensity-modulated excitation light is defined as f, a thickness of the stratum corneum indicated by the stratum corneum information is defined as d, and a thermal diffusion coefficient of the sample is defined as $\alpha$, the intensity modulation is performed so that f, d, and $\alpha$ satisfy $f<\alpha/(d^2\pi)$.

9. The component measurement method according to claim 8, wherein:
    the intensity modulation is performed so that f, d, and a further satisfy $\alpha/\{(3d)^2\pi\}<f$.

10. The component measurement method according to claim 6, wherein:
    the intensity modulation is performed by a rotary blade that rotates at a predetermined rotation speed and is disposed between the excitation light source and the optical medium portion,
    the excitation light is emitted onto the optical medium portion through the rotary blade, and
    the intensity modulation includes changing the rotation speed of the rotary blade based on the stratum corneum information.

11. The component measurement method according to claim 6, wherein:
    the intensity modulation includes performing modulation on a power source of the excitation light source based on the stratum corneum information.

* * * * *